US012612075B2

(12) United States Patent (10) Patent No.: US 12,612,075 B2
Notaro et al. (45) Date of Patent: Apr. 28, 2026

(54) DETERMINING EMOTIONAL STATE OF A VEHICLE OCCUPANT

(71) Applicant: GM Global Technology Operations LLC, Detroit, MI (US)

(72) Inventors: Gina Notaro, Los Angeles, CA (US); Mia Levy, Venice, CA (US); Evelyn Kim, Irvine, CA (US); Akilesh Rajavenkatanarayanan, Macomb, MI (US); Maureen Elizabeth August, Grosse Pointe Woods, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 317 days.

(21) Appl. No.: 18/425,277

(22) Filed: Jan. 29, 2024

(65) Prior Publication Data

US 2025/0242834 A1     Jul. 31, 2025

(51) Int. Cl.
*B60W 60/00*          (2020.01)
*A61B 5/00*          (2006.01)
(Continued)

(52) U.S. Cl.
CPC ......... *B60W 60/0013* (2020.02); *A61B 5/165* (2013.01); *A61B 5/167* (2013.01);
(Continued)

(58) Field of Classification Search
CPC .......... B60W 60/0013; B60W 2540/22; A61B 5/165; A61B 5/167; A61B 5/18; G06F 2203/011
See application file for complete search history.

(56) References Cited

U.S. PATENT DOCUMENTS 9,189,599 B2    11/2015   Adler et al.
9,507,413 B2    11/2016   Gee
(Continued)

FOREIGN PATENT DOCUMENTS

DE       102015101507 A1    8/2015
DE       102015200775 A1    7/2016
(Continued)

OTHER PUBLICATIONS

National Aeronautics and Space Administration (NASA). "Technology Solution: Sensors—Multivariate Monitoring for Human Operator and Machine Teaming," https://web.archive.org/web/20230928175836/https://technology.nasa.gov/patent/LAR-TOPS-301.

*Primary Examiner* — Donald J Wallace
(74) *Attorney, Agent, or Firm* — Vivacqua Crane, PLLC

(57) ABSTRACT
A method for increasing comfort of an occupant in a vehicle includes training a plurality of emotional state prediction machine learning models. The method further may include recording a plurality of sensor data using at least one vehicle sensor. The method further may include determining an occupant personality profile of the occupant. The method further may include selecting a selected one of the plurality of emotional state prediction machine learning models based at least in part on the occupant personality profile. The method further may include determining an occupant emotional state of the occupant based at least in part on the plurality of sensor data using the selected one of the plurality of emotional state prediction machine learning models. The method further may include adjusting an operation of a vehicle autonomous driving system of the vehicle based at least in part on the occupant emotional state.

20 Claims, 5 Drawing Sheets

(51) Int. Cl.

| | |
|---|---|
| *A61B 5/16* | (2006.01) |
| *A61B 5/18* | (2006.01) |
| *B60W 50/00* | (2006.01) |
| *B60W 50/14* | (2020.01) |

(52) U.S. Cl.
CPC .............. *A61B 5/18* (2013.01); *A61B 5/7267* (2013.01); *A61B 5/7275* (2013.01); *B60W 50/0097* (2013.01); *B60W 50/14* (2013.01); *A61B 2503/22* (2013.01); *B60W 2420/403* (2013.01); *B60W 2520/10* (2013.01); *B60W 2520/105* (2013.01); *B60W 2540/043* (2020.02); *B60W 2540/22* (2013.01); *B60W 2540/30* (2013.01); *B60W 2554/802* (2020.02)

(56) References Cited

U.S. PATENT DOCUMENTS

| | | | |
|---|---|---|---|
| 9,956,963 B2 | 5/2018 | Vijaya Kumar et al. |
| 10,614,388 B2 | 4/2020 | Reiner |
| 10,625,732 B2 | 4/2020 | Kim et al. |
| 10,835,168 B2 | 11/2020 | Flickinger |
| 10,997,526 B2 | 5/2021 | Harrivel et al. |
| 11,086,317 B2 | 8/2021 | Healey et al. |
| 11,783,228 B2 | 10/2023 | Harrivel et al. |
| 2015/0220068 A1* | 8/2015 | Goldman-Shenhar ...................... G05B 13/0265 700/47 |
| 2018/0061415 A1 | 3/2018 | Penilla et al. |
| 2019/0049957 A1* | 2/2019 | Healey .............. B60W 50/0098 |
| 2020/0311475 A1* | 10/2020 | el Kaliouby ........... G06N 3/045 |
| 2021/0269045 A1 | 9/2021 | Katz et al. |
| 2021/0272394 A1* | 9/2021 | Cella ...................... G06Q 40/08 |
| 2024/0034335 A1* | 2/2024 | Araki .................... B60W 40/09 |
| 2024/0227823 A9* | 7/2024 | Levy ........................ A61B 5/18 |
| 2024/0239349 A1* | 7/2024 | Degani ............. B60W 60/0013 |
| 2024/0362931 A1* | 10/2024 | Katz ................... G06V 40/20 |
| 2025/0222937 A1* | 7/2025 | Sharma .................. G06V 10/70 |

FOREIGN PATENT DOCUMENTS

| | | |
|---|---|---|
| DE | 112019001733 T5 | 12/2020 |
| DE | 102021101451 A1 | 7/2022 |
| DE | 102022127026 A1 | 4/2023 |
| DE | 102023120674 A1 | 7/2024 |

* cited by examiner

108a

108

108b

108

DETERMINING EMOTIONAL STATE OF A VEHICLE OCCUPANT

INTRODUCTION

The present disclosure relates to systems and methods for increasing occupant comfort, and more particularly, to systems and methods for increasing occupant comfort based at least in part on identifying an occupant's mood or emotional state.

To increase occupant awareness, vehicles may be equipped with driver monitoring systems (DMS). DMSs are configured to monitor one or more aspects of an occupant's mood or attentiveness in order to inform the operation of vehicle systems. In some embodiments, DMSs include one or more sensors (e.g., cameras) configured to monitor and/or measure one or more aspects of the occupant (e.g., facial expression, gaze direction, and/or the like). In a non-limiting example, the DMS may use signal processing algorithms to determine one or more aspects of the occupant's mood or attentiveness. For example, a DMS may be used to disable a Society of Automotive Engineers (SAE) LEVEL 3 automated driving system in response to determining that the occupant is not attentive to the roadway. In another example, a DMS may be used to monitor driver fatigue and suggest that the driver take a break from driving. However, current DMSs may not be configured to adaptively select signal processing algorithms based on an occupant's predispositions towards the vehicle or vehicle systems.

Thus, while current driver monitoring systems (DMS) achieve their intended purpose, there is a need for a new and improved system and method for increasing comfort of an occupant in a vehicle.

SUMMARY

According to several aspects, a method for increasing comfort of an occupant in a vehicle is provided. The method may include training a plurality of emotional state prediction machine learning models. The method further may include recording a plurality of sensor data using at least one vehicle sensor. The method further may include determining an occupant personality profile of the occupant. The method further may include selecting a selected one of the plurality of emotional state prediction machine learning models based at least in part on the occupant personality profile. The method further may include determining an occupant emotional state of the occupant based at least in part on the plurality of sensor data using the selected one of the plurality of emotional state prediction machine learning models. The method further may include adjusting an operation of a vehicle autonomous driving system of the vehicle based at least in part on the occupant emotional state.

In another aspect of the present disclosure, training the plurality of emotional state prediction machine learning models further may include determining the occupant personality profile of each of a plurality of training occupants. The occupant personality profile of each of the plurality of training occupants is selected from a plurality of personality profiles. At least one of the plurality of training occupants has each of the plurality of personality profiles. Training the plurality of emotional state prediction machine learning models further may include providing the plurality of training occupants with one or more simulated driving scenarios. Training the plurality of emotional state prediction machine learning models further may include recording a plurality of training sensor data sets. Each of the plurality of training sensor data sets corresponds to one of the plurality of training occupants. Training the plurality of emotional state prediction machine learning models further may include training the plurality of emotional state prediction machine learning models based at least in part on the plurality of training sensor data sets and the occupant personality profile of each of the plurality of training occupants. Each of the plurality of emotional state prediction machine learning models corresponds to one of the plurality of personality profiles. The plurality of emotional state prediction machine learning models are configured to receive the plurality of sensor data as an input and provide the occupant emotional state as an output.

In another aspect of the present disclosure, determining the occupant personality profile of each of the plurality of training occupants further may include conducting a survey of each of the plurality of training occupants. The survey includes one or more questions to determine a training occupant's disposition regarding the vehicle autonomous driving system of the vehicle. Determining the occupant personality profile of each of the plurality of training occupants further may include determining the occupant personality profile of each of the plurality of training occupants based at least in part on one or more answers of each of the plurality of training occupants to the one or more questions of the survey.

In another aspect of the present disclosure, training the plurality of emotional state prediction machine learning models further may include training a low-trust emotional state prediction machine learning model based on a first of the plurality of training sensor data sets corresponding to a first of the plurality of training occupants. The occupant personality profile of the first of the plurality of training occupants is a low-trust occupant personality profile. Training the plurality of emotional state prediction machine learning models further may include training a medium-trust emotional state prediction machine learning model based on a second of the plurality of training sensor data sets corresponding to a second of the plurality of training occupants. The occupant personality profile of the second of the plurality of training occupants is a medium-trust occupant personality profile. Training the plurality of emotional state prediction machine learning models further may include training a high-trust emotional state prediction machine learning model based on a third of the plurality of training sensor data sets corresponding to a third of the plurality of training occupants. The occupant personality profile of the third of the plurality of training occupants is a high-trust occupant personality profile.

In another aspect of the present disclosure, the method further includes training a personality profile identification machine learning model based at least in part on the plurality of sensor data of each of the plurality of training occupants and the occupant personality profile of each of the plurality of training occupants. The personality profile identification machine learning model is configured to determine the occupant personality profile based at least in part on the plurality of sensor data.

In another aspect of the present disclosure, determining the occupant personality profile of the occupant further may include conducting a survey of the occupant. The survey includes one or more questions to determine a disposition of the occupant regarding the vehicle autonomous driving system of the vehicle. Determining the occupant personality profile of the occupant further may include determining the occupant personality profile of the occupant based at least in part on at least one of: one or more answers of the occupant to the one or more questions of the survey and the personality profile identification machine learning model based at least in part on the plurality of sensor data.

In another aspect of the present disclosure, selecting the selected one of the plurality of emotional state prediction machine learning models based at least in part on the occupant personality profile further may include selecting a low-trust emotional state prediction machine learning model from the plurality of emotional state prediction machine learning models in response to determining that the occupant personality profile is a low-trust occupant personality profile. Selecting the selected one of the plurality of emotional state prediction machine learning models based at least in part on the occupant personality profile further may include selecting a medium-trust emotional state prediction machine learning model from the plurality of emotional state prediction machine learning models in response to determining that the occupant personality profile is a medium-trust occupant personality profile. Selecting the selected one of the plurality of emotional state prediction machine learning models based at least in part on the occupant personality profile further may include selecting a high-trust emotional state prediction machine learning model from the plurality of emotional state prediction machine learning models in response to determining that the occupant personality profile is a high-trust occupant personality profile.

In another aspect of the present disclosure, determining the occupant emotional state further may include executing the selected one of the plurality of emotional state prediction machine learning models. The selected one of the plurality of emotional state prediction machine learning models is provided with the plurality of sensor data as an input. The selected one of the plurality of emotional state prediction machine learning models provides the occupant emotional state as an output. The occupant emotional state includes at least one of: a low-stress emotional state, a medium-stress emotional state, and a high-stress emotional state.

In another aspect of the present disclosure, adjusting the operation of the vehicle autonomous driving system of the vehicle further may include adjusting one or more driving parameters of the vehicle autonomous driving system in response to determining that the occupant emotional state is at least one of: the high-stress emotional state and the medium-stress emotional state.

In another aspect of the present disclosure, adjusting the one or more driving parameters of the vehicle autonomous driving system further may include adjusting the one or more driving parameters of the vehicle autonomous driving system in response to determining that the occupant emotional state is at least one of: the high-stress emotional state and the medium-stress emotional state. The one or more driving parameters includes at least one of: a driving speed, a driving aggressiveness, a following distance, a maximum acceleration limit, and an activation state of an advanced driver assistance feature.

According to several aspects, a system for increasing comfort of an occupant in a vehicle is provided. The system may include at least one vehicle sensor. The at least one vehicle sensor is operable to capture data about the occupant. The system further may include a vehicle autonomous driving system. The system further may include a vehicle controller in electrical communication with the at least one vehicle sensor and the vehicle autonomous driving system. The vehicle controller is programmed to record a plurality of sensor data using the at least one vehicle sensor. The vehicle controller is further programmed to determine an occupant personality profile of the occupant based at least in part on the plurality of sensor data. The occupant personality profile is one of a plurality of personality profiles. The vehicle controller is further programmed to select a selected one of a plurality of emotional state prediction machine learning models based at least in part on the occupant personality profile. Each of the plurality of emotional state prediction machine learning models corresponds to one of the plurality of personality profiles. The vehicle controller is further programmed to determine an occupant emotional state of the occupant based at least in part on the plurality of sensor data using the selected one of the plurality of emotional state prediction machine learning models. The vehicle controller is further programmed to adjust an operation of the vehicle autonomous driving system based at least in part on the occupant emotional state.

In another aspect of the present disclosure, the at least one vehicle sensor includes at least a camera configured to view a face of the occupant.

In another aspect of the present disclosure, to determine the occupant personality profile, the vehicle controller is further programmed to conduct a survey of the occupant. The survey includes one or more questions to determine a disposition of the occupant regarding the vehicle autonomous driving system. To determine the occupant personality profile, the vehicle controller is further programmed to determine the occupant personality profile of the occupant based at least in part on at least one of: one or more answers of the occupant to the one or more questions of the survey and a personality profile identification machine learning model based at least in part on the plurality of sensor data.

In another aspect of the present disclosure, to select the selected one of a plurality of emotional state prediction machine learning models, the vehicle controller is further programmed to select a low-trust emotional state prediction machine learning model from the plurality of emotional state prediction machine learning models in response to determining that the occupant personality profile is a low-trust occupant personality profile. To select the selected one of a plurality of emotional state prediction machine learning models, the vehicle controller is further programmed to select a medium-trust emotional state prediction machine learning model from the plurality of emotional state prediction machine learning models in response to determining that the occupant personality profile is a medium-trust occupant personality profile. To select the selected one of a plurality of emotional state prediction machine learning models, the vehicle controller is further programmed to select a high-trust emotional state prediction machine learning model from the plurality of emotional state prediction machine learning models in response to determining that the occupant personality profile is a high-trust occupant personality profile.

In another aspect of the present disclosure, to determine the occupant emotional state, the vehicle controller is further programmed to execute the selected one of the plurality of emotional state prediction machine learning models. The selected one of the plurality of emotional state prediction machine learning models is provided with the plurality of sensor data as an input. The selected one of the plurality of emotional state prediction machine learning models provides the occupant emotional state as an output. The occupant emotional state includes at least one of: a low-stress emotional state, a medium-stress emotional state, and a high-stress emotional state.

In another aspect of the present disclosure, to adjust the operation of the vehicle autonomous driving system, the vehicle controller is further programmed to adjust one or more driving parameters of the vehicle autonomous driving system in response to determining that the occupant emotional state is at least one of: the high-stress emotional state and the medium-stress emotional state. The one or more driving parameters includes at least one of: a driving speed, a driving aggressiveness, a following distance, a maximum acceleration limit, and an activation state of an advanced driver assistance feature.

In another aspect of the present disclosure, the plurality of emotional state prediction machine learning models is trained based at least in part on a plurality of training sensor data sets. Each of the plurality of training sensor data sets corresponds to one of the plurality of personality profiles.

According to several aspects, a method for increasing comfort of an occupant in a vehicle is provided. The method may include recording a plurality of sensor data using at least one vehicle sensor. The method further may include determining an occupant personality profile of the occupant. The method further may include selecting a selected one of a plurality of emotional state prediction machine learning models based at least in part on the occupant personality profile. The method further may include determining an occupant emotional state of the occupant based at least in part on the plurality of sensor data using the selected one of the plurality of emotional state prediction machine learning models. The method further may include adjusting an operation of a vehicle autonomous driving system of the vehicle based at least in part on the occupant emotional state.

In another aspect of the present disclosure, the method further includes determining the occupant personality profile of each of a plurality of training occupants. The occupant personality profile of each of the plurality of training occupants is selected from a plurality of personality profiles. At least one of the plurality of training occupants has each of the plurality of personality profiles. The method further includes providing the plurality of training occupants with one or more simulated driving scenarios. The method further includes recording a plurality of training sensor data sets. Each of the plurality of training sensor data sets corresponds to one of the plurality of training occupants. The method further includes training the plurality of emotional state prediction machine learning models based at least in part on the plurality of training sensor data sets and the occupant personality profile of each of the plurality of training occupants. Each of the plurality of emotional state prediction machine learning models corresponds to one of the plurality of personality profiles. The plurality of emotional state prediction machine learning models are configured to receive the plurality of sensor data as an input and provide the occupant emotional state as an output.

In another aspect of the present disclosure, training the plurality of emotional state prediction machine learning models further may include training a low-trust emotional state prediction machine learning model based on a first of the plurality of training sensor data sets corresponding to a first of the plurality of training occupants. The occupant personality profile of the first of the plurality of training occupants is a low-trust occupant personality profile. Training the plurality of emotional state prediction machine learning models further may include training a medium-trust emotional state prediction machine learning model based on a second of the plurality of training sensor data sets corresponding to a second of the plurality of training occupants. The occupant personality profile of the second of the plurality of training occupants is a medium-trust occupant personality profile. Training the plurality of emotional state prediction machine learning models further may include training a high-trust emotional state prediction machine learning model based on a third of the plurality of training sensor data sets corresponding to a third of the plurality of training occupants. The occupant personality profile of the third of the plurality of training occupants is a high-trust occupant personality profile.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

In aspects of the present disclosure, in-vehicle sensors may be used to identify a mood or emotional state of an occupant in order to determine the occupant's comfort with actions of a vehicle autonomous driving system. However, vehicle occupants may have different predispositions regarding trust and confidence in vehicle autonomous driving systems, and emotional state identification without regard for occupant predispositions may be less accurate. Therefore, the present disclosure provides a new and improved system and method to identify an occupant emotional state with regard to occupant predispositions about vehicle autonomous driving systems, allowing for actions to increase occupant comfort.

Figure 1:
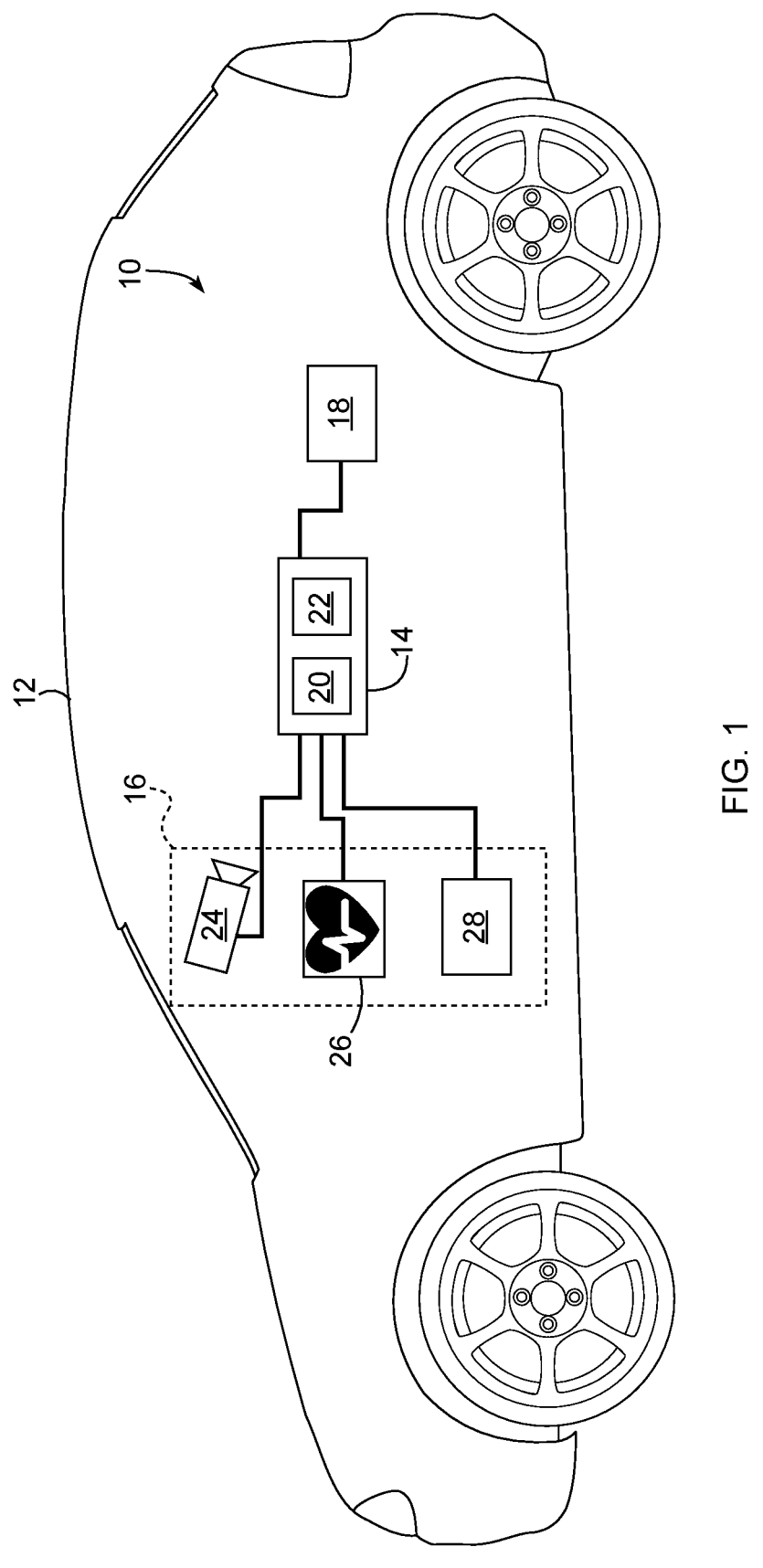
FIG. 1 is a schematic diagram of a system for increasing comfort of an occupant in a vehicle, according to an exemplary embodiment.

Referring to FIG. 1, a system for increasing comfort of an occupant in a vehicle is illustrated and generally indicated by reference number 10. The system 10 is shown with an exemplary vehicle 12. While a passenger vehicle is illustrated, it should be appreciated that the vehicle 12 may be any type of vehicle without departing from the scope of the present disclosure. The system 10 generally includes a vehicle controller 14, at least one vehicle sensor 16, and a vehicle autonomous driving system 18.

The vehicle controller 14 is used to implement a method 100 for increasing comfort of an occupant in a vehicle, as will be described below. The vehicle controller 14 includes at least one processor 20 and a non-transitory computer readable storage device or media 22. The processor 20 may be a custom made or commercially available processor, a central processing unit (CPU), a graphics processing unit (GPU), an auxiliary processor among several processors associated with the vehicle controller 14, a semiconductor-based microprocessor (in the form of a microchip or chip set), a macroprocessor, a combination thereof, or generally a device for executing instructions. The computer readable storage device or media 22 may include volatile and non-volatile storage in read-only memory (ROM), random-access memory (RAM), and keep-alive memory (KAM), for example. KAM is a persistent or non-volatile memory that may be used to store various operating variables while the processor 20 is powered down. The computer-readable storage device or media 22 may be implemented using a number of memory devices such as PROMs (programmable read-only memory), EPROMs (electrically PROM), EEPROMs (electrically erasable PROM), flash memory, or another electric, magnetic, optical, or combination memory devices capable of storing data, some of which represent executable instructions, used by the vehicle controller 14 to control various systems of the vehicle 12. The vehicle controller 14 may also consist of multiple controllers which are in electrical communication with each other. The vehicle controller 14 may be inter-connected with additional systems and/or controllers of the vehicle 12, allowing the vehicle controller 14 to access data such as, for example, speed, acceleration, braking, and steering angle of the vehicle 12.

The vehicle controller 14 is in electrical communication with the at least one vehicle sensor 16 and the vehicle autonomous driving system 18. In an exemplary embodiment, the electrical communication is established using, for example, a controller area network (CAN) network, a FLEXRAY network, a local area network (e.g., WiFi, ethernet, and the like), a serial peripheral interface (SPI) network, or the like. It should be understood that various additional wired and wireless techniques and communication protocols for communicating with the vehicle controller 14 are within the scope of the present disclosure.

The at least one vehicle sensor 16 is used to acquire information about the occupant of the vehicle 12. In the scope of the present disclosure, the occupant includes, in a non-limiting example, a driver, a passenger, and/or any additional persons in the vehicle 12. In an exemplary embodiment, the at least one vehicle sensor 16 includes at least a camera 24. In another exemplary embodiment, the at least one vehicle sensor 16 further includes a biometric sensor 26. In another exemplary embodiment, the at least one vehicle sensor further includes one or more additional sensors 28. The at least one vehicle sensor 16 is in electrical communication with the vehicle controller 14, as discussed above.

The camera 24 is used to capture images and/or videos of the occupant within the vehicle 12. In an exemplary embodiment, the camera 24 is a photo and/or video camera which is positioned to view a face of the occupant within the vehicle 12. In one example, the camera 24 is affixed in a headliner of the vehicle 12, having a view of the occupant of the vehicle 12. In another example, the camera 24 is affixed in, on, or near a dashboard of the vehicle 12, having a view of the occupant of the vehicle 12. In an exemplary embodiment, the camera 24 is used to capture one or more images of the face of the occupant, allowing for determination of an emotional state of the occupant based at least in part on the one or more images, as is discussed in greater detail below.

In some embodiments, the camera 24 is part of a driver monitoring system (DMS). In a non-limiting example, a DMS is a system which uses sensors (e.g., the camera 24) to monitor and analyze the occupant's behavior to ensure alertness, attentiveness, and/or the like. It should be understood that the camera 24 may include multiple cameras disposed in multiple locations throughout the vehicle 12 without departing from the scope of the present disclosure. It should further be understood that cameras having various sensor types including, for example, charge-coupled device (CCD) sensors, complementary metal oxide semiconductor (CMOS) sensors, and/or high dynamic range (HDR) sensors are within the scope of the present disclosure. Furthermore, cameras having various lens types including, for example, wide-angle lenses and/or narrow-angle lenses are also within the scope of the present disclosure. The camera 24 is in electrical communication with the vehicle controller 14, as discussed above.

The biometric sensor 26 is used to perform biometric measurements of the occupant. In the scope of the present disclosure, biometric measurements include, for example, respiration rate, heart rate, galvanic skin response, blood oxygen, body temperature, pupil dilation, brain activity, and/or the like. In an exemplary embodiment, the biometric sensor 26 includes at least one of: a respiration rate sensor, a heart rate sensor, a galvanic skin response sensor, an electroencephalography (EEG) sensor, and/or the like. The biometric sensor 26 is in electrical communication with the vehicle controller 14, as discussed above.

In a non-limiting example, the respiration rate sensor is used to measure a respiration (i.e., breathing) rate of the occupant. In an exemplary embodiment, the respiration rate sensor is a pneumograph affixed to a chest or abdomen of the occupant. In another exemplary embodiment, the respiration rate sensor is a non-contact, infrared respiration rate sensor affixed within the vehicle 12. In an exemplary embodiment, variations in respiration rate may be associated with emotional state of the occupant. For example, an increased respiration rate may indicate negative emotions such as stress or anger.

In a non-limiting example, the heart rate sensor is used to measure a heart rate of the occupant. In an exemplary embodiment, the heart rate sensor is an electrical sensor operable to detect a bio-electrical potential generated by electrical signals which control the expansion and contraction of heart chambers. In another exemplary embodiment, the heart rate sensor is an optical sensor which uses light-based technology to measure a blood volume conveyed by the heart's pumping action. In a non-limiting example, the heart rate sensor is disposed within a seat, armrest, steering wheel, and/or other surface typically in contact with the occupant within the vehicle 12. In an exemplary embodiment, variations in heart rate may be associated with emotional state of the occupant. For example, an increased heart rate may indicate negative emotions such as stress or anger.

In a non-limiting example, the galvanic skin response sensor is used to measure a skin conductivity of the occupant. In an exemplary embodiment, the galvanic skin response sensor is an electrical sensor operable to measure an electrical conductance between multiple electrodes in contact with the occupant's skin. In a non-limiting example, the galvanic skin response sensor is disposed within a seat, armrest, steering wheel, and/or other surface typically in contact with the occupant within the vehicle 12. In an exemplary embodiment, variations in skin conductivity (i.e., galvanic skin response) may be associated with emotional state of the occupant. For example, an increased skin conductance may indicate negative emotions such as stress, anger, or anxiety.

In a non-limiting example, the EEG sensor is used to measure brain wave activity of the occupant. In a non-limiting example, the EEG sensor is disposed within a headrest of the vehicle 12. In an exemplary embodiment, different patterns of brain waves may be associated with emotional state of the occupant.

The one or more additional sensors 28 are used to capture additional information about the occupant. In an exemplary embodiment, the one or more additional sensors 28 include at least one of: a thermal imaging sensor operable to determine a skin temperature of the occupant (e.g., a facial skin temperature), a functional near-infrared spectroscopy (fNIRS) device, and an eye-tracker operable to determine pupil diameter and eye gaze direction. The one or more additional sensors 28 are in electrical communication with the vehicle controller 14, as discussed above.

The vehicle autonomous driving system 18 is used to provide assistance to the occupant to increase occupant awareness and/or control behavior of the vehicle 12. In the scope of the present disclosure, the vehicle autonomous driving system 18 encompasses systems which provide any level of assistance to the occupant (e.g., blind spot warning, lane departure warning, and/or the like) and systems which are capable of autonomously driving the vehicle 12 under some or all conditions (e.g., automated lane keeping, adaptive cruise control, fully autonomous driving, and/or the like). It should be understood that all levels of driving automation defined by, for example, Society of Automotive Engineers (SAE) J3016 (i.e., SAE LEVEL 0, SAE LEVEL 1, SAE LEVEL 2, SAE LEVEL 3, SAE LEVEL 4, and SAE LEVEL 5) are within the scope of the present disclosure.

In an exemplary embodiment, the vehicle autonomous driving system 18 is configured to detect and/or receive information about the environment surrounding the vehicle 12 and process the information to provide assistance to the occupant. In some embodiments, the vehicle autonomous driving system 18 is a software module executed on the vehicle controller 14. In other embodiments, the vehicle autonomous driving system 18 includes a separate autonomous driving system controller, similar to the vehicle controller 14, capable of processing the information about the environment surrounding the vehicle 12. In an exemplary embodiment, the vehicle autonomous driving system 18 may operate in a manual operation mode, a partially automated operation mode, and a fully automated operation mode.

In the scope of the present disclosure, the manual operation mode means that the vehicle autonomous driving system 18 provides warnings or notifications to the occupant but does not intervene or control the vehicle 12 directly. In a non-limiting example, the vehicle autonomous driving system 18 receives information from one or more perception sensors (i.e., one or more sensors operable to perceive information about the environment surrounding the vehicle 12, such as, for example, one or more exterior cameras, a LIDAR sensor, a vehicle communication system, a global navigation satellite system, and/or the like). Using techniques such as, for example, computer vision, the vehicle autonomous driving system 18 understands the environment surrounding the vehicle 12 and provides assistance to the occupant. For example, if the vehicle autonomous driving system 18 identifies, based on data from the one or more perception sensors (e.g., one or more exterior cameras, a LIDAR sensor, a vehicle communication system, a global navigation satellite system, and/or the like), that the vehicle 12 is likely to collide with a remote vehicle, the vehicle autonomous driving system 18 may use a display to provide a warning to the occupant.

In the scope of the present disclosure, the partially automated operation mode means that the vehicle autonomous driving system 18 provides warnings or notifications to the occupant and may intervene or control the vehicle 12 directly in certain situations. In a non-limiting example, the vehicle autonomous driving system 18 is additionally in electrical communication with components of the vehicle 12 such as a brake system, a propulsion system (e.g., an internal combustion engine and/or an electric drivetrain), and/or a steering system of the vehicle 12, such that the vehicle autonomous driving system 18 may control the behavior of the vehicle 12. In a non-limiting example, the vehicle autonomous driving system 18 may control the behavior of the vehicle 12 by applying brakes of the vehicle 12 to avoid an imminent collision.

In another non-limiting example, the vehicle autonomous driving system 18 may control the steering system of the vehicle 12 to provide an automated lane keeping feature. In another non-limiting example, the vehicle autonomous driving system 18 may control the brake system, propulsion system, and steering system of the vehicle 12 to temporarily drive the vehicle 12 towards a predetermined destination. However, intervention by the occupant may be required at any time. In an exemplary embodiment, the vehicle autonomous driving system 18 may include additional components such as, for example, a driver monitoring system (DMS) including, for example, an eye tracking device configured to monitor an attention level of the occupant and ensure that the occupant is prepared to take over control of the vehicle 12.

In the scope of the present disclosure, the fully automated operation mode means that the vehicle autonomous driving system 18 uses data from one or more perception sensors (e.g., one or more exterior cameras, a LIDAR sensor, a vehicle communication system, a global navigation satellite system, and/or the like) to understand the environment and control the vehicle 12 to drive the vehicle 12 to a predetermined destination without a need for control or intervention by the occupant.

The vehicle autonomous driving system 18 operates using a path planning algorithm which is configured to generate a safe and efficient trajectory for the vehicle 12 to navigate in the environment surrounding the vehicle 12. In an exemplary embodiment, the path planning algorithm is a machine learning model trained to output control signals for the vehicle 12 based on input data collected from the one or more perception sensors (e.g., one or more exterior cameras, a LIDAR sensor, a vehicle communication system, a global navigation satellite system, and/or the like). In another exemplary embodiment, the path planning algorithm is a deterministic algorithm which has been programmed to output control signals for the vehicle 12 based on data collected from the one or more perception sensors (e.g., one or more exterior cameras, a LIDAR sensor, a vehicle communication system, a global navigation satellite system, and/or the like).

In a non-limiting example, the path planning algorithm generates a sequence of waypoints or a continuous path that the vehicle 12 should follow to reach a destination while adhering to rules, regulations, and safety constraints. The sequence of waypoints or continuous path is generated based at least in part on a detailed map and a current state of the vehicle 12 (i.e., position, velocity, and orientation of the vehicle 12). The detailed map includes, for example, information about lane boundaries, road geometry, speed limits, traffic signs, and/or other relevant features. In an exemplary embodiment, the detailed map is stored in the media 22 of the vehicle controller 14 and/or on a remote database or server. In another exemplary embodiment, the path planning algorithm performs perception and mapping tasks to interpret data collected from the one or more perception sensors (e.g., one or more exterior cameras, a LIDAR sensor, a vehicle communication system, a global navigation satellite system, and/or the like) and create, update, and/or augment the detailed map.

In an exemplary embodiment, one or more aspects of the operation of the vehicle autonomous driving system 18 are defined by one or more driving parameters of the vehicle autonomous driving system 18. In a non-limiting example, the driving parameters include, for example, a driving speed (i.e., a percentage of the road speed limit which the vehicle autonomous driving system 18 drives under normal conditions), a minimum following distance behind remote vehicles, a maximum acceleration limit, and/or the operation mode of the vehicle autonomous driving system 18 (i.e., the manual operation mode, the partially automated operation mode, or the fully automated operation mode). The value of one or more of the aforementioned driving parameters may contribute to an overall driving aggressiveness of the vehicle autonomous driving system 18. The driving aggressiveness may be understood as a propensity of the vehicle autonomous driving system 18 to take actions which are perceived by the occupant as risky (e.g., pulling into traffic with a minimal gap/following distance).

In an exemplary embodiment, the driving parameters are controllable by at least the vehicle controller 14 in response to, for example, weather/roadway conditions, safety margins, laws/regulations, vehicle autonomous driving system 18 status, vehicle performance capability, occupant preference, occupant emotional state (as is discussed in greater detail below), and/or the like. It should be understood that the vehicle autonomous driving system 18 may include any software and/or hardware module configured to operate in any combination of the manual operation mode, the partially automated operation mode, or the fully automated operation mode as described above. The vehicle autonomous driving system 18 is in electrical communication with the vehicle controller 14, as discussed above.

Figure 2:
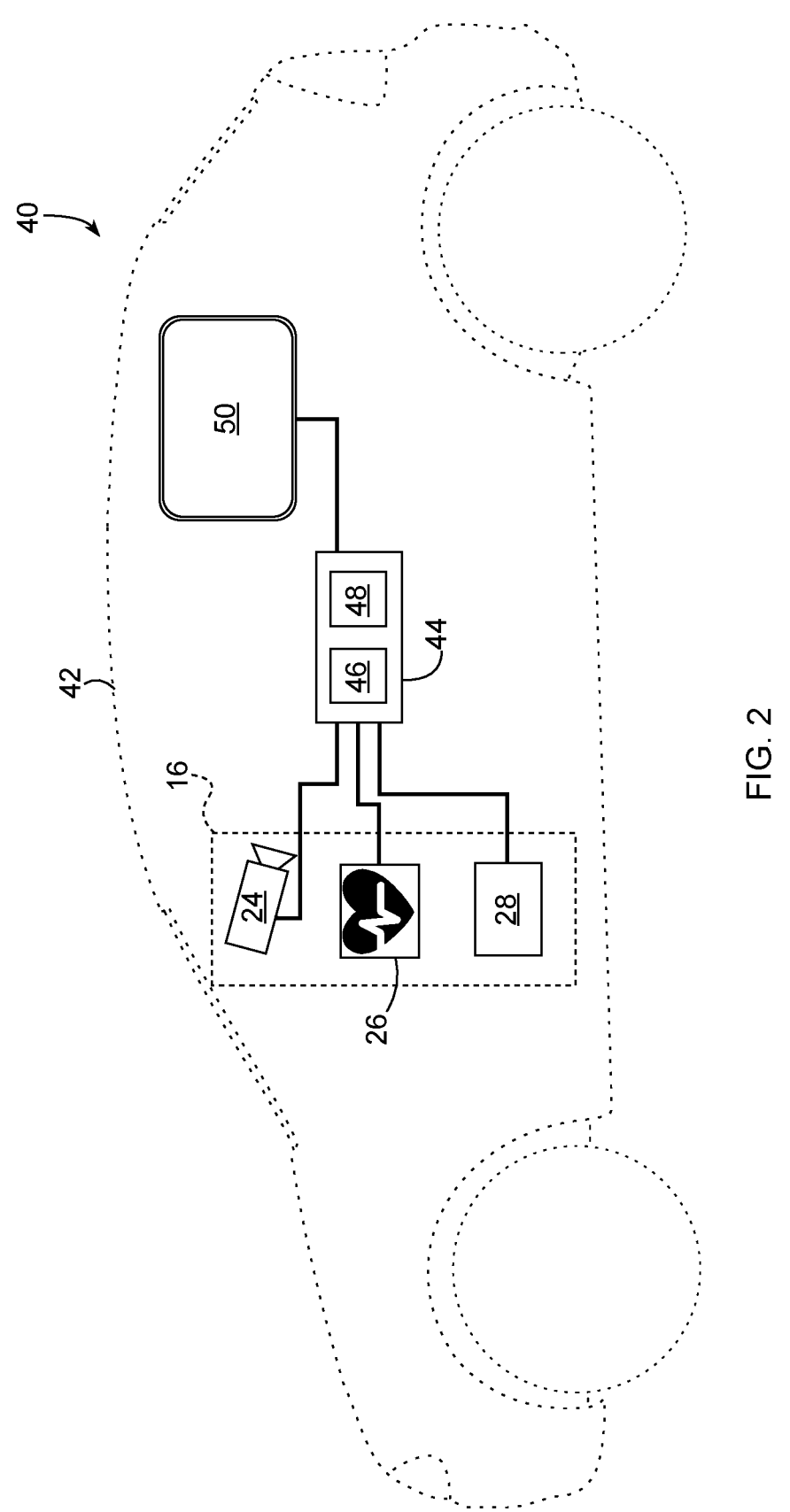
FIG. 2 is a schematic diagram of a driving simulation system, according to an exemplary embodiment.

Referring to FIG. 2, a schematic diagram of a driving simulation system 40 is shown. The driving simulation system 40 is used to train machine learning models by providing simulated driving scenarios to a plurality of training occupants, as is discussed in greater detail below. The driving simulation system 40 includes a driving simulator 42. The driving simulator 42 is a structure which allows for simulation of driving scenarios for training occupants. In an exemplary embodiment, the driving simulator 42 is a substantially stationary structure configured to look and feel like an interior of the vehicle 12. In a non-limiting example, the driving simulator 42 includes a steering wheel, a dashboard, control pedals (e.g., a brake pedal and an accelerator pedal), one or more occupant seats, and/or the like.

The driving simulator 42 further includes the at least one vehicle sensor 16. The at least one vehicle sensor 16 in the driving simulator 42 is affixed and configured in the driving simulator 42 in a similar manner as in the vehicle 12. The driving simulator 42 further includes a simulator controller 44 and a simulator display 50. The simulator controller 44 includes at least one simulator processor 46 and a simulator non-transitory computer readable storage device or simulator media 48. The description of the type and configuration given above for the vehicle controller 14 also applies to the simulator controller 44. In some examples, the simulator controller 44 may differ from the vehicle controller 14 in that the simulator controller 44 is capable of a higher processing speed, includes more memory, includes more inputs/outputs, and/or the like. In a non-limiting example, the simulator processor 46 and simulator media 48 of the simulator controller 44 are similar in structure and/or function to the processor 20 and the media 22 of the vehicle controller 14, as described above.

The simulator controller 44 is in electrical communication with the at least one vehicle sensor 16 of the driving simulator 42 and the simulator display 50. In an exemplary embodiment, the electrical communication is established using, for example, a controller area network (CAN) network, a FLEXRAY network, a local area network (e.g., WiFi, ethernet, and the like), a serial peripheral interface (SPI) network, or the like. It should be understood that various additional wired and wireless techniques and communication protocols for communicating with the simulator controller 44 are within the scope of the present disclosure.

The simulator display 50 is used to display one or more simulated driving scenarios. In an exemplary embodiment, the simulator display is disposed within the driving simulator 42 such as to mimic a view through a windscreen of the vehicle 12. In a non-limiting example, the simulator controller 44 retrieves one or more videos of simulated driving scenarios from the simulator media 48 and displays the one or more videos of the simulated driving scenarios using the simulator display 50.

Figure 3:
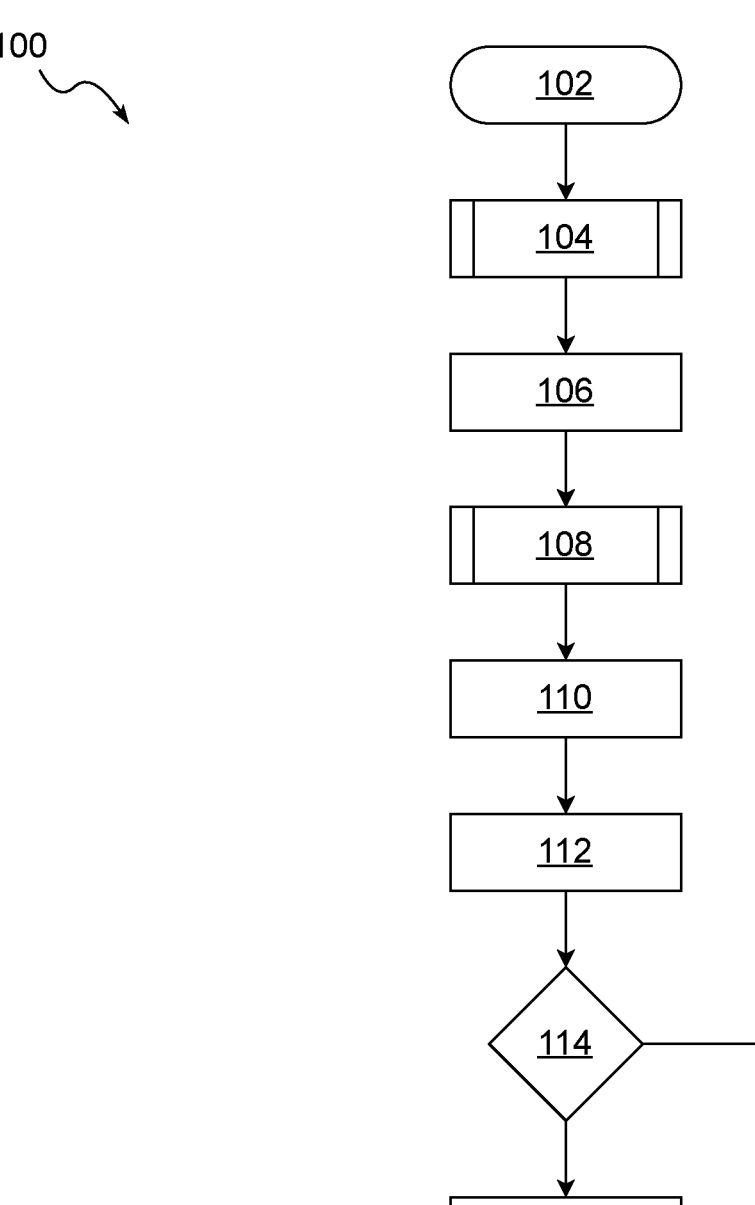
FIG. 3 is a flowchart of the method for increasing comfort of an occupant in a vehicle, according to an exemplary embodiment.

Referring to FIG. 3, a flowchart of the method 100 for increasing comfort of an occupant in a vehicle is shown. The method 100 begins at block 102 and proceeds to block 104. At block 104 a plurality of emotional state prediction machine learning models are trained. In an exemplary embodiment, the plurality of emotional state prediction machine learning models includes a low-trust emotional state prediction machine learning model, a medium-trust emotional state prediction machine learning model, and a high-trust emotional state prediction machine learning model. It should be understood that the plurality of emotional state prediction machine learning models may include various additional emotional state prediction machine learning models with different parameters and characteristics without departing from the scope of the present disclosure. Training of the plurality of emotional state prediction machine learning models is discussed in greater detail below. After block 104, the method 100 proceeds to block 106.

At block 106, the vehicle controller 14 uses the at least one vehicle sensor 16 to record a plurality of sensor data. In the scope of the present disclosure, the plurality of sensor data includes sensor data about the occupant, including, for example, sensor data captured by the camera 24, the biometric sensor 26, and/or the one or more additional sensors 28. In a non-limiting example, the sensor data about the occupant includes one or more images of the face of the occupant captured by the camera 24, a respiration rate, a heart rate, a galvanic skin response, a blood oxygen, a body temperature, a pupil dilation, a brain activity, and/or the like captured by the biometric sensor 26, a skin temperature of the occupant, a pupil diameter of the occupant, and/or an eye gaze direction of the occupant captured by the one or more additional sensors 28, and/or the like. In an exemplary embodiment, the plurality of sensor data is stored in the media 22 of the vehicle controller 14 for later retrieval. After block 106, the method 100 proceeds to block 108.

At block 108, the vehicle controller 14 determines an occupant personality profile of the occupant. In the scope of the present disclosure, the occupant personality profile of the occupant is a metric which describes the occupant's disposition regarding the vehicle autonomous driving system 18 (i.e., the occupant's level of trust in, comfortability with, and/or confidence in the vehicle autonomous driving system 18). In an exemplary embodiment, the occupant personality profile is selected from a plurality of personality profiles. In an exemplary embodiment, the plurality of personality profiles includes at least: a low-trust occupant personality profile, a medium-trust occupant personality profile, and high-trust occupant personality profile. It should be understood that the plurality of personality profiles may include various additional personality profiles without departing from the scope of the present disclosure. The determination of the occupant personality profile is discussed in greater detail below. After block 108, the method 100 proceeds to block 110.

At block 110, the vehicle controller 14 selects one of the plurality of emotional state prediction machine learning models trained at block 104 (referred to hereinafter as the selected one of the plurality of emotional state prediction machine learning models). In an exemplary embodiment, the vehicle controller 14 selects the selected one of the plurality of emotional state prediction machine learning models based at least in part on the occupant personality profile determined at block 108. In a non-limiting example, the vehicle controller 14 selects the low-trust emotional state prediction machine learning model in response to determining that the occupant personality profile is the low-trust occupant personality profile. The vehicle controller 14 selects the medium-trust emotional state prediction machine learning model in response to determining that the occupant personality profile is the medium-trust occupant personality profile. The vehicle controller 14 selects the high-trust emotional state prediction machine learning model in response to determining that the occupant personality profile is the high-trust occupant personality profile. It should be understood that the vehicle controller 14 may select various additional emotional state prediction machine learning models in the plurality of emotional state prediction machine learning models without departing from the scope of the present disclosure. After block 110, the method 100 proceeds to block 112.

At block 112, the vehicle controller 14 determines an emotional state of the occupant (hereinafter referred to as an occupant emotional state). In the scope of the present disclosure, the occupant emotional state is a metric which describes a level of negative emotion (e.g., stress, worry, confusion, fear, anger, and/or the like) of the occupant. In an exemplary embodiment, the occupant emotional state is quantified as a value on a continuous scale (e.g., a continuous scale between zero and one hundred, where zero indicates very little negative emotion, and one hundred indicates extremely high negative emotion).

In another exemplary embodiment, the occupant emotional state includes at least one of: a low-stress emotional state, a medium-stress emotional state, and a high-stress emotional state. In the scope of the present disclosure, the low-stress emotional state describes an occupant who is exhibiting little to no negative emotion. In the scope of the present disclosure, the medium-stress emotional state describes an occupant who is exhibiting a moderate level of negative emotion. In the scope of the present disclosure, the high-stress emotional state describes an occupant who is exhibiting a high level of negative emotion.

In an exemplary embodiment, to determine the occupant emotional state, the vehicle controller 14 executes the selected one of the plurality of emotional state prediction machine learning models selected at block 110. In an exemplary embodiment, the selected one of the plurality of emotional state prediction machine learning models is provided with the plurality of sensor data recorded at block 106 as an input and provides the occupant emotional state as an output. The plurality of emotional state prediction machine learning models is discussed in greater detail below. After block 112, the method 100 proceeds to block 114.

At block 114, in an exemplary embodiment, if the occupant emotional state determined at block 112 and quantified on the continuous scale is less than a predetermined emotional state threshold, the method 100 proceeds to enter a standby state at block 116. If the occupant emotional state determined at block 112 and quantified on the continuous scale is greater than or equal to the predetermined emotional state threshold, the method 100 proceeds to block 118, as is discussed in greater detail below. In another exemplary embodiment, if the occupant emotional state determined at block 112 is the low-stress emotional state, the method 100 proceeds to enter the standby state at block 116. If the occupant emotional state determined at block 112 is the medium-stress emotional state or the high-stress emotional state, the method 100 proceeds to block 118.

At block 118, the vehicle controller 14 adjusts the operation of the vehicle autonomous driving system 18. In an exemplary embodiment, to adjust the operation of the vehicle autonomous driving system 18, the vehicle controller 14 adjusts the driving parameters of the vehicle autonomous driving system 18. The vehicle controller 14 adjusts the driving parameters of the vehicle autonomous driving system 18 to improve the occupant emotional state (i.e., decrease the level of negative emotion of the occupant). In a non-limiting example, the vehicle controller 14 decreases the driving speed, increases the minimum following distance behind remote vehicles, decreases the maximum acceleration limit, and/or decreases the driving aggressiveness.

In another exemplary embodiment, the vehicle controller 14 takes additional actions to improve the occupant emotional state. In a non-limiting example, the vehicle controller 14 uses a display of the vehicle 12 to provide a notification to the occupant about the functioning of the vehicle autonomous driving system 18. In a non-limiting example, the vehicle controller 14 adjusts an operation of a vehicle heating, ventilation, and air conditioning (HVAC) system. In a non-limiting example, the vehicle controller 14 adjusts an operation of vehicle interior cabin lighting. In a non-limiting example, the vehicle controller 14 adjusts an operation of a vehicle regenerative braking system. In a non-limiting example, the vehicle controller 14 adjusts an operation of a global navigation satellite system (GNSS) of the vehicle 12 (e.g., suggesting an alternative navigation routing to a destination). In a non-limiting example, the vehicle controller 14 adjusts an activation state (i.e., an enablement or disablement) of an advanced driver assistance feature (e.g., a lane keeping assistance feature, an adaptive cruise control feature, a forward collision alert feature, and/or the like). It should be understood that the vehicle controller 14 may take further actions to improve the emotional state of the occupant without departing from the scope of the present disclosure. After block 118, the method 100 proceeds to enter the standby state at block 116.

In an exemplary embodiment, the vehicle controller 14 repeatedly exits the standby state 116 and restarts the method 100 at block 102. In a non-limiting example, the vehicle controller 14 exits the standby state 116 and restarts the method 100 on a timer, for example, every three hundred milliseconds.

Figure 4:
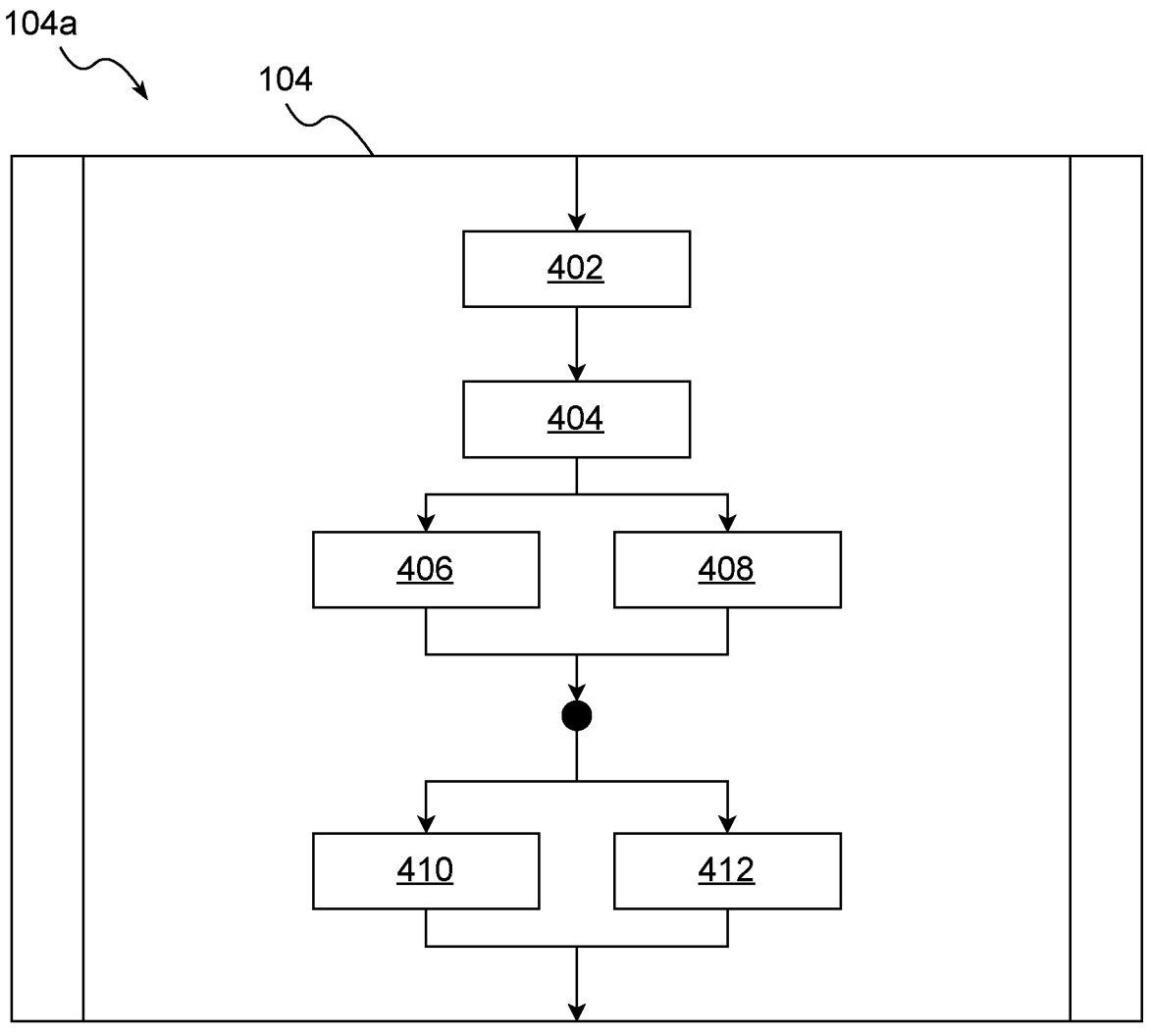
FIG. 4 is a flowchart of a method for training a plurality of emotional state prediction machine learning models, according to an exemplary embodiment.

Referring to FIG. 4, a flowchart of an exemplary embodiment 104a of block 104 (i.e., a method for training the plurality of emotional state prediction machine learning models) is shown. It should be understood that the exemplary embodiment 104a may be performed with any computerized system capable of providing simulated driving scenarios. It should further be understood that the exemplary embodiment 104a may be performed using crowdsourced data from actual vehicles and/or occupants. In an exemplary embodiment discussed hereinafter, the exemplary embodiment 104a is performed with the driving simulator system 40 and a plurality of training occupants.

In the scope of the present disclosure, the plurality of training occupants includes a plurality of driving-age individuals having varying backgrounds, personalities, driving experience, and/or experience with automated driving systems. In a non-limiting example, the plurality of training occupants is substantially representative of the general driving population. The exemplary embodiment 104a begins at block 402. At block 402, the simulator controller 44 determines the occupant personality profile of each of the plurality of training occupants. In an exemplary embodiment, to determine the occupant personality profile of each of the plurality of training occupants, the simulator controller 44 conducts a survey of each of the plurality of training occupants. In a non-limiting example, the survey includes one or more questions to determine a training occupant's disposition regarding the vehicle autonomous driving system 18 (i.e., the occupant's level of trust in, comfortability with, and/or confidence in the vehicle autonomous driving system 18). In an exemplary embodiment, the survey contains a plurality of questions, each of which the training occupant may respond to with one of: very inaccurate, moderately inaccurate, neither accurate nor inaccurate, moderate accurate, or very accurate.

A set of exemplary survey questions is shown below in Table 1. In a non-limiting example, the exemplary survey includes twenty-eight questions divided into three categories: agentic capability, synchronized mental model, and autonomy propensity to use.

In an exemplary embodiment, the survey is presented to each of the plurality of training occupants using the simulator display 50 and the answers are saved in the simulator media 48 of the simulator controller 44. In another exemplary embodiment, the survey is provided to each of the plurality of training occupants outside of the simulation system 40 (e.g., online or on paper) and the answers are subsequently loaded into the simulator media 48 of the simulator controller 44. After block 402, the exemplary embodiment 104a proceeds to block 404.

At block 404, the simulator controller 44 determines the occupant personality profile of each of the plurality of training occupants based at least in part on one or more answers of each of the plurality of training occupants to the one or more questions of the survey conducted at block 402. In an exemplary embodiment, to determine the occupant personality profile, the simulator controller 44 uses a deterministic algorithm based directly on the answers to the survey to categorize each of the plurality of occupants as having the low-trust occupant personality profile, the medium-trust occupant personality profile, or the high-trust occupant personality profile.

In another exemplary embodiment, to determine the occupant personality profile, the simulator controller 44 uses a machine learning model trained to categorize each of the plurality of occupants as having the low-trust occupant personality profile, the medium-trust occupant personality profile, or the high-trust occupant personality profile based at least in part on the answers to the survey. After block 404, the exemplary embodiment 104a proceeds to blocks 406 and 408.

At block 406, the simulator controller 44 uses the simulator display 50 to provide each of the plurality of training occupants with one or more simulated driving scenarios. In a non-limiting example, the one or more simulated driving scenarios include scenarios with varying weather conditions, varying traffic conditions, varying road conditions, and/or the like. In a non-limiting example, the one or more simulated driving scenarios include scenarios where a simulated autonomous driving system controls a behavior of the simulated vehicle. In a non-limiting example, the one or more simulated driving scenarios include at least one known non-stress-inducing scenario (e.g., a simulated drive down

TABLE 1

| Set of exemplary survey questions. | | |
| --- | --- | --- |
| Agentic Capability<br>The autonomous agent . . . | Synchronized Mental Model<br>The autonomous agent . . . | Autonomy Propensity to Use |
| 1. Has the ability to make some decisions on its own | 11. Is generally on the "same page" as me | 19. The automobile provides security |
| 2. Has the authority to make decisions | 12. Gets me what I need before I ask for it | 20. The automobile behaves in an unexpected manner |
| 3. Has the capability to control its actions | 13. . . . and I feel out of step with one another | 21. I am suspicious of the automobile's intent or actions |
| 4. Always seems to need my help | 14. Is engaged with me throughout the entire task | 22. I am confident in the automobile |
| 5. Does not require me to control it 100% of the time | 15. Reacts in expected ways | 23. I am wary of the automobile |
| 6. Can perform its tasks autonomously | 16. Adapts to new situations as when I do | 24. The automobile is dependable |
| 7. Is in control of its own actions | 17. Anticipates my actions | 25. The automobile is reliable |
| 8. Executes the best course of action | 18. Anticipates my needs | 26. The automobile's action can have harmful or injurious outcome |
| 9. Requires me to monitor it | | 27. I can trust the automobile |
| 10. Can operate with little to no oversight | | 28. I am at ease while riding in the automobile | an open road in good weather conditions with no traffic) and at least one known stress-inducing scenario (e.g., a simulated drive in poor weather conditions at high speed with high traffic volume). After block 406, the exemplary embodiment 104a proceeds to blocks 410 and 412, as is discussed in greater detail below.

At block 408, simultaneously to the playback of the simulated driving scenarios at block 406, the simulator controller 44 records a training sensor data set for each of the plurality of training occupants (i.e., a plurality of training sensor data sets). In an exemplary embodiment, each of the plurality of training sensor data sets includes data captured of one of the plurality of training occupants from the one or more vehicle sensor 16 in the simulator 42 during the one or more simulated driving scenarios. After block 408, the exemplary embodiment 104a proceeds to blocks 410 and 412.

At block 410, the simulator controller 44 trains the plurality of emotional state prediction machine learning models based at least in part on the plurality of training sensor data sets collected at block 408, the occupant personality profile of each of the plurality of training occupants determined at block 404, and the content of the one or more simulated driving scenarios. In an exemplary embodiment, the content of the one or more simulated driving scenarios provides ground-truth information for training. For example, a training occupant's physiological response (as measured by the one or more vehicle sensors 16) during playback of the known non-stress-inducing driving scenario may serve as a baseline for identification of the low-stress emotional state. In another example, a training occupant's physiological response (as measured by the one or more vehicle sensors 16) during playback of the known stress-inducing driving scenario may serve as a baseline for identification of the high-stress emotional state.

In an exemplary embodiment, each of the plurality of emotional state prediction machine learning models is trained using one or more of the plurality of training sensor data sets from training occupants having a same occupant personality profile. In a non-limiting example, the low-trust emotional state prediction machine learning model is trained based on a first of the plurality of training sensor data sets corresponding to a first of the plurality of training occupants, wherein the occupant personality profile of the first of the plurality of training occupants is the low-trust occupant personality profile. In a non-limiting example, the medium-trust emotional state prediction machine learning model is trained based on a second of the plurality of training sensor data sets corresponding to a second of the plurality of training occupants, wherein the occupant personality profile of the second of the plurality of training occupants is a medium-trust occupant personality profile. In a non-limiting example, the high-trust emotional state prediction machine learning model is trained based on a third of the plurality of training sensor data sets corresponding to a third of the plurality of training occupants, wherein the occupant personality profile of the third of the plurality of training occupants is a high-trust occupant personality profile.

The following description of the function and training of an emotional state prediction machine learning model is applicable to each of the plurality of emotional state prediction machine learning models, provided that each of the plurality of emotional state prediction machine learning models is trained using one or more of the plurality of training sensor data sets from training occupants having a same occupant personality profile, as discussed above. In a non-limiting example, the emotional state prediction machine learning model includes multiple layers, including an input layer and an output layer, as well as one or more hidden layers. The emotional state prediction machine learning model receives the plurality of sensor data recorded at block 106 as inputs. The inputs are then passed on to the hidden layers. Each hidden layer applies a transformation (e.g., a non-linear transformation) to the data and passes the result to the next hidden layer until the final hidden layer. The output layer produces the occupant emotional state.

To train the emotional state prediction machine learning model, a subset of the plurality of training sensor data sets collected at block 408 and the content of the one or more simulated driving scenarios is used. The content of the one or more simulated driving scenarios provides ground-truth information, as discussed above. The algorithm is trained by adjusting internal weights between nodes in each hidden layer to minimize prediction error. During training, an optimization technique (e.g., gradient descent) is used to adjust the internal weights to reduce the prediction error. The training process is repeated until the prediction error is minimized, and the resulting trained model is then used to classify new input data.

After sufficient training of the emotional state prediction machine learning model, the algorithm is capable of accurately and precisely determining occupant emotional state based on the plurality of sensor data recorded at block 106. By adjusting the weights between the nodes in each hidden layer during training, the algorithm "learns" to recognize patterns in the sensor data that are indicative of occupant emotional state. In an exemplary embodiment, each of the plurality of emotional state prediction machine learning models is loaded into the media 22 of the vehicle controller 14 for use by the vehicle controller 14. In a non-limiting example, each of the plurality of emotional state prediction machine learning models may be further trained and/or re-trained using real-world data gathered by the vehicle controller 14 to improve an accuracy of each of the plurality of emotional state prediction machine learning models. After block 410, the exemplary embodiment 104a is concluded, and the method 100 proceeds as discussed above.

At block 412, the simulator controller 44 trains a personality profile identification machine learning model. In the scope of the present disclosure, the personality profile identification machine learning model is configured to determine the occupant personality profile based at least in part on the plurality of sensor data recorded at block 106, thereby allowing determination of the occupant personality profile without surveying each occupant.

In a non-limiting example, the personality profile identification machine learning model includes multiple layers, including an input layer and an output layer, as well as one or more hidden layers. The personality profile identification machine learning model receives the plurality of sensor data recorded at block 106 as inputs. The inputs are then passed on to the hidden layers. Each hidden layer applies a transformation (e.g., a non-linear transformation) to the data and passes the result to the next hidden layer until the final hidden layer. The output layer produces the occupant personality profile.

To train the personality profile identification machine learning model, the plurality of training sensor data sets collected at block 408 and the occupant personality profile of each of the plurality of training occupants determined based on one or more answers of each of the plurality of training occupants to the one or more questions of the survey conducted at block 402 are used. The algorithm is trained by adjusting internal weights between nodes in each hidden layer to minimize prediction error. During training, an optimization technique (e.g., gradient descent) is used to adjust the internal weights to reduce the prediction error. The training process is repeated until the prediction error is minimized, and the resulting trained model is then used to classify new input data.

After sufficient training of the personality profile identification machine learning model, the algorithm is capable of accurately and precisely determining occupant personality profile based on the plurality of sensor data recorded at block 106. By adjusting the weights between the nodes in each hidden layer during training, the algorithm "learns" to recognize patterns in the sensor data that are indicative of occupant emotional state. In an exemplary embodiment, the personality profile identification machine learning model is loaded into the media 22 of the vehicle controller 14 for use by the vehicle controller 14. In a non-limiting example, the personality profile identification machine learning model may be further trained and/or re-trained using real-world data gathered by the vehicle controller 14 to improve an accuracy of the personality profile identification machine learning model. After block 412, the exemplary embodiment 104a is concluded, and the method 100 proceeds as discussed above.

Figure 5A:
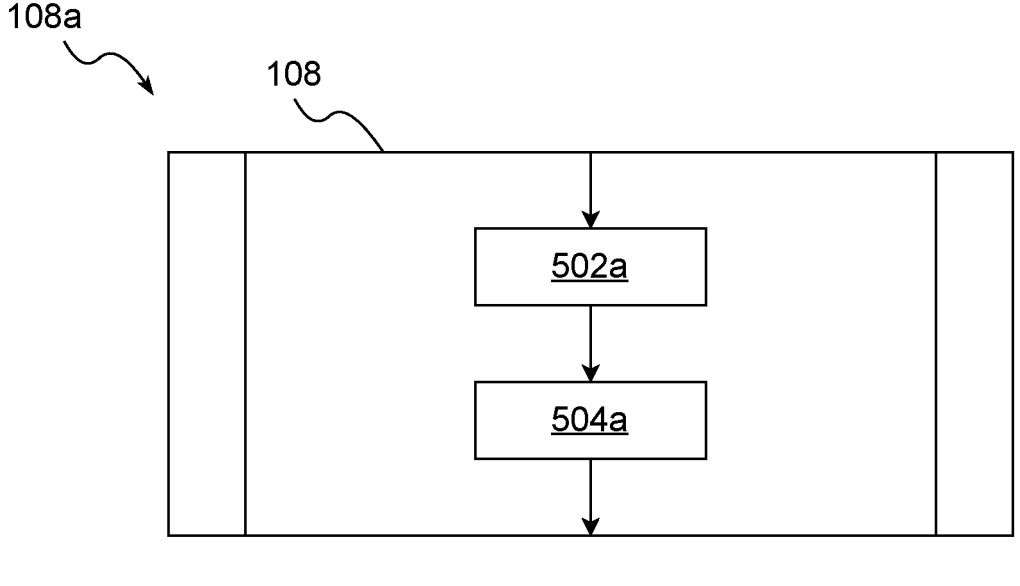
FIG. 5A is a flowchart of a first exemplary embodiment of a method for determining an occupant personality profile of an occupant, according to an exemplary embodiment.

Referring to FIG. 5A, a flowchart of a first exemplary embodiment 108a of block 108 (i.e., a method for determining the occupant personality profile of the occupant) is shown. The first exemplary embodiment 108a begins at block 502a. At block 502a, the vehicle controller 14 conducts a survey of the occupant. In a non-limiting example, the survey is conducted upon a new occupant's first entry into the vehicle 12. In another non-limiting example, the survey is periodically re-conducted at regular and/or irregular intervals. In a non-limiting example, the survey includes one or more questions to determine a training occupant's disposition regarding the vehicle autonomous driving system 18 (i.e., the occupant's level of trust in, comfortability with, and/or confidence in the vehicle autonomous driving system 18). In an exemplary embodiment, the survey contains a plurality of questions, each of which the training occupant may respond to with one of: very inaccurate, moderately inaccurate, neither accurate nor inaccurate, moderate accurate, or very accurate. A set of exemplary survey questions is shown above in Table 1.

In an exemplary embodiment, the survey is presented to the occupant using a display of the vehicle 12 and the answers are saved in the media 22 of the vehicle controller 14. In another exemplary embodiment, the survey is provided to occupant outside of the vehicle 12 (e.g., on a mobile device) and the answers are subsequently loaded into the media 22 of the vehicle controller 14. After block 502a, the first exemplary embodiment 108a proceeds to block 504a.

At block 504a, the vehicle controller 14 determines the occupant personality profile of the occupant based at least in part on one or more answers of the occupant to the one or more questions of the survey conducted at block 504a. In an exemplary embodiment, to determine the occupant personality profile, the vehicle controller 14 uses a deterministic algorithm based directly on the answers to the survey to categorize each of the plurality of occupants as having the low-trust occupant personality profile, the medium-trust occupant personality profile, or the high-trust occupant personality profile.

In another exemplary embodiment, to determine the occupant personality profile, the vehicle controller 14 uses a machine learning model trained to categorize each of the plurality of occupants as having the low-trust occupant personality profile, the medium-trust occupant personality profile, or the high-trust occupant personality profile based at least in part on the answers to the survey. After block 504a, the first exemplary embodiment 108a is concluded, and the method 100 proceeds as discussed above.

Figure 5B:
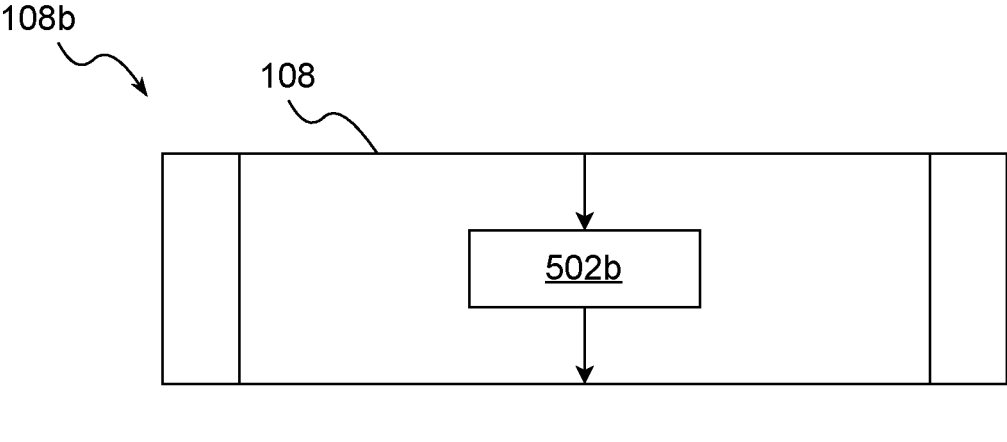
FIG. 5B is a flowchart of a second exemplary embodiment of a method for determining an occupant personality profile of an occupant, according to an exemplary embodiment.

Referring to FIG. 5B, a flowchart of a second exemplary embodiment 108b of block 108 (i.e., a method for determining the occupant personality profile of the occupant) is shown. The second exemplary embodiment 108b begins at block 502b. At block 502b, the vehicle controller 14 uses the personality profile identification machine learning model trained at block 412 to determine the occupant personality profile based at least in part on the plurality of sensor data recorded at block 106. After block 502b, the second exemplary embodiment 108b is concluded, and the method 100 proceeds as discussed above.

It should be understood that either the first exemplary embodiment 108a of block 108, the second exemplary embodiment 108b of block 108, or both may be used to determine the occupant personality profile of the occupant during execution of block 108 in the method 100.

The system 10 and method 100 of the present disclosure offer several advantages. By evaluating an occupant's disposition towards the vehicle autonomous driving system 18 (i.e., the occupant personality profile) and using a corresponding one of the plurality of emotional state prediction machine learning models to determine the occupant emotional state, the precision and accuracy of emotional state prediction based on sensor data is increased. Furthermore, the system 10 and method 100 may be used to re-evaluate the occupant personality profile at periodic intervals and/or in response to changing sensor data indicating a change in occupant personality profile. Subsequently, the vehicle controller 14 may take action to improve occupant comfort based on the occupant emotional state. Finally, the system 10 and method 100 are applicable to various additional manned automated vehicles, such as, for example, partially/fully automated aircraft.

The description of the present disclosure is merely exemplary in nature and variations that do not depart from the gist of the present disclosure are intended to be within the scope of the present disclosure. Such variations are not to be regarded as a departure from the spirit and scope of the present disclosure.

What is claimed is:

1. A method for increasing comfort of an occupant in a vehicle, the method comprising:
   training a plurality of emotional state prediction machine learning models;
   recording a plurality of sensor data using at least one vehicle sensor;
   determining an occupant personality profile of the occupant;
   selecting a selected one of the plurality of emotional state prediction machine learning models based at least in part on the occupant personality profile;
   determining an occupant emotional state of the occupant based at least in part on the plurality of sensor data using the selected one of the plurality of emotional state prediction machine learning models; and
   adjusting an operation of a vehicle autonomous driving system of the vehicle based at least in part on the occupant emotional state.

2. The method of claim 1, wherein training the plurality of emotional state prediction machine learning models further comprises:

determining the occupant personality profile of each of a plurality of training occupants, wherein the occupant personality profile of each of the plurality of training occupants is selected from a plurality of personality profiles, and wherein at least one of the plurality of training occupants has each of the plurality of personality profiles;

providing the plurality of training occupants with one or more simulated driving scenarios;

recording a plurality of training sensor data sets, wherein each of the plurality of training sensor data sets corresponds to one of the plurality of training occupants; and training the plurality of emotional state prediction machine learning models based at least in part on the plurality of training sensor data sets and the occupant personality profile of each of the plurality of training occupants, wherein each of the plurality of emotional state prediction machine learning models corresponds to one of the plurality of personality profiles, and wherein the plurality of emotional state prediction machine learning models are configured to receive the plurality of sensor data as an input and provide the occupant emotional state as an output.

3. The method of claim 2, wherein determining the occupant personality profile of each of the plurality of training occupants further comprises:

conducting a survey of each of the plurality of training occupants, wherein the survey includes one or more questions to determine a training occupant's disposition regarding the vehicle autonomous driving system of the vehicle; and determining the occupant personality profile of each of the plurality of training occupants based at least in part on one or more answers of each of the plurality of training occupants to the one or more questions of the survey.

4. The method of claim 2, wherein training the plurality of emotional state prediction machine learning models further comprises:

training a low-trust emotional state prediction machine learning model based on a first of the plurality of training sensor data sets corresponding to a first of the plurality of training occupants, wherein the occupant personality profile of the first of the plurality of training occupants is a low-trust occupant personality profile;

training a medium-trust emotional state prediction machine learning model based on a second of the plurality of training sensor data sets corresponding to a second of the plurality of training occupants, wherein the occupant personality profile of the second of the plurality of training occupants is a medium-trust occupant personality profile; and training a high-trust emotional state prediction machine learning model based on a third of the plurality of training sensor data sets corresponding to a third of the plurality of training occupants, wherein the occupant personality profile of the third of the plurality of training occupants is a high-trust occupant personality profile.

5. The method of claim 2, further comprising:

training a personality profile identification machine learning model based at least in part on the plurality of sensor data of each of the plurality of training occupants and the occupant personality profile of each of the plurality of training occupants, wherein the personality profile identification machine learning model is configured to determine the occupant personality profile based at least in part on the plurality of sensor data.

6. The method of claim 5, wherein determining the occupant personality profile of the occupant further comprises:

conducting a survey of the occupant, wherein the survey includes one or more questions to determine a disposition of the occupant regarding the vehicle autonomous driving system of the vehicle; and determining the occupant personality profile of the occupant based at least in part on at least one of: one or more answers of the occupant to the one or more questions of the survey and the personality profile identification machine learning model based at least in part on the plurality of sensor data.

7. The method of claim 1, wherein selecting the selected one of the plurality of emotional state prediction machine learning models based at least in part on the occupant personality profile further comprises:

selecting a low-trust emotional state prediction machine learning model from the plurality of emotional state prediction machine learning models in response to determining that the occupant personality profile is a low-trust occupant personality profile;

selecting a medium-trust emotional state prediction machine learning model from the plurality of emotional state prediction machine learning models in response to determining that the occupant personality profile is a medium-trust occupant personality profile; and selecting a high-trust emotional state prediction machine learning model from the plurality of emotional state prediction machine learning models in response to determining that the occupant personality profile is a high-trust occupant personality profile.

8. The method of claim 1, wherein determining the occupant emotional state further comprises:

executing the selected one of the plurality of emotional state prediction machine learning models, wherein the selected one of the plurality of emotional state prediction machine learning models is provided with the plurality of sensor data as an input, wherein the selected one of the plurality of emotional state prediction machine learning models provides the occupant emotional state as an output, and wherein the occupant emotional state includes at least one of: a low-stress emotional state, a medium-stress emotional state, and a high-stress emotional state.

9. The method of claim 8, wherein adjusting the operation of the vehicle autonomous driving system of the vehicle further comprises:

adjusting one or more driving parameters of the vehicle autonomous driving system in response to determining that the occupant emotional state is at least one of: the high-stress emotional state and the medium-stress emotional state.

10. The method of claim 9, wherein adjusting the one or more driving parameters of the vehicle autonomous driving system further comprises:

adjusting the one or more driving parameters of the vehicle autonomous driving system in response to determining that the occupant emotional state is at least one of: the high-stress emotional state and the medium-stress emotional state, wherein the one or more driving parameters includes at least one of: a driving speed, a driving aggressiveness, a following distance, a maximum acceleration limit, and an activation state of an advanced driver assistance feature.

11. A system for increasing comfort of an occupant in a vehicle, the system comprising:

at least one vehicle sensor, wherein the at least one vehicle sensor is operable to capture data about the occupant;

a vehicle autonomous driving system; and a vehicle controller in electrical communication with the at least one vehicle sensor and the vehicle autonomous driving system, wherein the vehicle controller is programmed to:

record a plurality of sensor data using the at least one vehicle sensor;

determine an occupant personality profile of the occupant based at least in part on the plurality of sensor data, wherein the occupant personality profile is one of a plurality of personality profiles;

select a selected one of a plurality of emotional state prediction machine learning models based at least in part on the occupant personality profile, wherein each of the plurality of emotional state prediction machine learning models corresponds to one of the plurality of personality profiles;

determine an occupant emotional state of the occupant based at least in part on the plurality of sensor data using the selected one of the plurality of emotional state prediction machine learning models; and adjust an operation of the vehicle autonomous driving system based at least in part on the occupant emotional state.

12. The system of claim 11, wherein the at least one vehicle sensor includes at least a camera configured to view a face of the occupant.

13. The system of claim 11, wherein to determine the occupant personality profile, the vehicle controller is further programmed to:

conduct a survey of the occupant, wherein the survey includes one or more questions to determine a disposition of the occupant regarding the vehicle autonomous driving system; and determine the occupant personality profile of the occupant based at least in part on at least one of: one or more answers of the occupant to the one or more questions of the survey and a personality profile identification machine learning model based at least in part on the plurality of sensor data.

14. The system of claim 13, wherein to select the selected one of a plurality of emotional state prediction machine learning models, the vehicle controller is further programmed to:

select a low-trust emotional state prediction machine learning model from the plurality of emotional state prediction machine learning models in response to determining that the occupant personality profile is a low-trust occupant personality profile;

select a medium-trust emotional state prediction machine learning model from the plurality of emotional state prediction machine learning models in response to determining that the occupant personality profile is a medium-trust occupant personality profile; and select a high-trust emotional state prediction machine learning model from the plurality of emotional state prediction machine learning models in response to determining that the occupant personality profile is a high-trust occupant personality profile.

15. The system of claim 14, wherein to determine the occupant emotional state, the vehicle controller is further programmed to:

execute the selected one of the plurality of emotional state prediction machine learning models, wherein the selected one of the plurality of emotional state prediction machine learning models is provided with the plurality of sensor data as an input, wherein the selected one of the plurality of emotional state prediction machine learning models provides the occupant emotional state as an output, and wherein the occupant emotional state includes at least one of: a low-stress emotional state, a medium-stress emotional state, and a high-stress emotional state.

16. The system of claim 15, wherein to adjust the operation of the vehicle autonomous driving system, the vehicle controller is further programmed to:

adjust one or more driving parameters of the vehicle autonomous driving system in response to determining that the occupant emotional state is at least one of: the high-stress emotional state and the medium-stress emotional state, wherein the one or more driving parameters includes at least one of: a driving speed, a driving aggressiveness, a following distance, a maximum acceleration limit, and an activation state of an advanced driver assistance feature.

17. The system of claim 11, wherein the plurality of emotional state prediction machine learning models is trained based at least in part on a plurality of training sensor data sets, wherein each of the plurality of training sensor data sets corresponds to one of the plurality of personality profiles.

18. A method for increasing comfort of an occupant in a vehicle, the method comprising:

recording a plurality of sensor data using at least one vehicle sensor;

determining an occupant personality profile of the occupant;

selecting a selected one of a plurality of emotional state prediction machine learning models based at least in part on the occupant personality profile;

determining an occupant emotional state of the occupant based at least in part on the plurality of sensor data using the selected one of the plurality of emotional state prediction machine learning models; and adjusting an operation of a vehicle autonomous driving system of the vehicle based at least in part on the occupant emotional state.

19. The method of claim 18, further comprising:

determining the occupant personality profile of each of a plurality of training occupants, wherein the occupant personality profile of each of the plurality of training occupants is selected from a plurality of personality profiles, and wherein at least one of the plurality of training occupants has each of the plurality of personality profiles;

providing the plurality of training occupants with one or more simulated driving scenarios;

recording a plurality of training sensor data sets, wherein each of the plurality of training sensor data sets corresponds to one of the plurality of training occupants; and training the plurality of emotional state prediction machine learning models based at least in part on the plurality of training sensor data sets and the occupant personality profile of each of the plurality of training occupants, wherein each of the plurality of emotional state prediction machine learning models corresponds to one of the plurality of personality profiles, and wherein the plurality of emotional state prediction machine learning models are configured to receive the plurality of sensor data as an input and provide the occupant emotional state as an output.

20. The method of claim 19, wherein training the plurality of emotional state prediction machine learning models further comprises:

training a low-trust emotional state prediction machine learning model based on a first of the plurality of training sensor data sets corresponding to a first of the plurality of training occupants, wherein the occupant personality profile of the first of the plurality of training occupants is a low-trust occupant personality profile;

training a medium-trust emotional state prediction machine learning model based on a second of the plurality of training sensor data sets corresponding to a second of the plurality of training occupants, wherein the occupant personality profile of the second of the plurality of training occupants is a medium-trust occupant personality profile; and training a high-trust emotional state prediction machine learning model based on a third of the plurality of training sensor data sets corresponding to a third of the plurality of training occupants, wherein the occupant personality profile of the third of the plurality of training occupants is a high-trust occupant personality profile.

\* \* \* \* \*